United States Patent

Vrespa

Patent Number: 5,593,410
Date of Patent: Jan. 14, 1997

[54] SCREW DEVICE FOR FIXING PROSTHESES TO BONES

[76] Inventor: Giuseppe Vrespa, Via C. Battisti 26, 20025 Legnano, Italy

[21] Appl. No.: 25,119

[22] Filed: Mar. 2, 1993

Related U.S. Application Data

[62] Division of Ser. No. 601,416, Oct. 22, 1990.

[30] Foreign Application Priority Data

Oct. 26, 1989 [IT] Italy ................................ 22139/89

[51] Int. Cl.⁶ .................................................. A61F 5/04
[52] U.S. Cl. ....................................................... 606/73
[58] Field of Search ................................ 606/65, 66, 73, 606/69, 72; 411/413

[56] References Cited

U.S. PATENT DOCUMENTS

| | | | |
|---|---|---|---|
| 2,243,717 | 5/1941 | Moreira | 606/65 |
| 2,414,882 | 1/1947 | Longfellow | 606/65 |
| 4,027,573 | 6/1977 | Laverty | 411/413 |
| 4,059,102 | 11/1977 | Devas | 606/72 X |
| 4,431,416 | 2/1984 | Niznick | 433/174 |
| 4,463,753 | 8/1984 | Gustilo | 606/73 |
| 4,858,601 | 8/1989 | Glisson | 606/65 X |
| 4,959,064 | 9/1990 | Engelhardt | 606/65 |
| 5,019,079 | 5/1991 | Ross | 606/73 X |
| 5,061,181 | 10/1991 | Niznick | 433/174 |
| 5,078,607 | 1/1992 | Niznick | 433/174 |
| 5,085,660 | 2/1992 | Lin | 606/73 |
| 5,094,618 | 3/1992 | Sullivan | 433/173 |
| 5,116,337 | 5/1992 | Johnson | 606/73 |
| 5,145,372 | 9/1992 | Daftary et al. | 433/174 X |
| 5,199,873 | 4/1993 | Schulte et al. | 433/174 |

FOREIGN PATENT DOCUMENTS

| | | | |
|---|---|---|---|
| 0724137 | 4/1990 | U.S.S.R. | 606/65 |
| 9109572 | 7/1991 | WIPO | 606/65 |

*Primary Examiner*—Debra S. Brittingham
*Attorney, Agent, or Firm*—Ladas & Parry

[57] ABSTRACT

In a screw device (10; 80) for fixing prostheses to bones, the threaded shank (14) comprises a core (32, 34) of overall frustoconical shape. The screw has a cylindrical neck (12) of diameter equal to or greater than the maximum diameter of the thread. This latter is of two different types, namely a first thread (26) of large pitch for fixing into the trabecular bone tissue (52) and a second thread (28), which can be of the self-tapping type, for fixing into tile cortical bone opposite the point at which the screw is inserted into the bone. The second thread (28) has a number of starts which is a multiple of that of the first thread (26). For orthopedic use the screw (80) can comprise a third thread (128) on a part of the neck (112) for fixing into the relative cortical bone (50). A method for applying the screw device (10; 80) consists of forming a precision hole (40) in the bone, tapping said hole with a tapper (60; 100), and screwing the screw (10; 80) into it. The precision hole (40) is obtained by using a cutter (100) in the shape of an inverted "wedding cake", then reaming the obtained cavity with a manual reamer (140).

10 Claims, 4 Drawing Sheets

SCREW DEVICE FOR FIXING PROSTHESES TO BONES

This is a divisional of co-pending application Ser. No. 07/601,416 filed Oct. 22, 1990.

DESCRIPTION

This invention relates to means for fixing prostheses to bones, and more specifically to screw devices for effecting this fixing. The invention also relates to a method for applying said screw device and the relative instrument for the application. As is well known, in terms of mechanical characteristics bone tissue can be divided into two distinct regions, namely the cortical bone region with an elastic modulus of between 1000 and 1200 dN/mm$^2$ and the spongy region, of trabecular bone tissue containing medulla or fat, with an elastic modulus of roughly between 20 and 400 dN/mm$^2$.

Currently, to execute an implant in any bone, use is made of known bone screws which have a substantially cylindrical shank and are constructed of a biocompatible metal such as titanium, austenitic stainless steel, tantalum, niobium or zirconium. These screws require a cylindrical hole to be previously drilled in the bone. If the screws are of the self-tapping type they are inserted directly into the cavity thus obtained, which always has a diameter less or at most equal to the core of the screw. In the case of non self-tapping screws the relative female thread has to be formed in the side surface of the hole.

For fixing purposes, known screws utilize either the mechanical characteristics of the trabecula and therefore have a thread of rather large pitch, of the type suitable for fairly soft materials, or the mechanical characteristics of the cortical bone opposite the point of penetration of the screw, which has a thread pitch significantly less than in the previous case and suitable for ensuring a good mechanical grip in hard materials, but not suitable for gripping tile trabecular bone tissue.

In its turn, because of its thinness the cotical region of the bone can generally only receive one large-pitch turn. In addition, because of its relative fragility: the cortical bone tissue is unsuitable for receiving a large-pitch thread.

This applies particularly; to the cortical bone located on the same side as that from which the self-tapping screw or thread tapper is inserted. In this respect, as stated the thread of the screw or tapper has a diameter greater than that of the drilled hole. In addition the screw neck (ie the cylindrical end of the screw to which the prosthesis is fixed, and which is normally not threaded but enters the cortical bone) has a diameter less than that of the thread. As a result, on inserting the self-tapping screw or tapper into the drilled hole the most outer part, ie the cortical bone, of the bone tissue is removed. Consequently, once the screw has been inserted into the bone, an empty annular space remains around the screw neck. This means that the cortical bone is surgically damaged for a certain area around the screw neck. The damage is directly proportional to the size of the tooth of the thread on the self-tapping screw or tapper. That part of the cortical bone which has been thus removed does not form again.

This represents a serious drawback as the cortical bone is the strongest region of the bone and the most suitable for supporting loads, particularly loads perpendicular to the screw axis. The cavity for receiving the screw is formed by rotary tools mounted on hand-controlled drills.

The shape and dimensions of the cavity obtained depend on various factors, and in particular:
a) the bone to be drilled;
b) the drilling tool;
c) the operator holding the drilling tool.

The causes influencing these three factors ill be examined in detail:
a) The bone to be drilled cannot be fixed rigidly, with the result that there is a certain freedom of movement. It also has a smooth, moist and therefore slippery surface. In addition the surface is somewhat round. Again, the structure is anisotropic so that the resistance offered to the tool cutting edge varies as drilling proceeds.
b) The drilling system comprises a drill bit or cutter of various shapes, such as a spade tip with a solid cylindrical body, a flared tip with a vertically grooved body to collect shavings, or a flared tip with a helically grooved body to collect shavings. No studies appear to have been carried out with the purpose of determining the best cutting angle for the bone, or conceiving a good system for discharging the bone shavings which mix with the blood and tend to coagulate. As is well known, when the drill bit is fitted into the drill it is retained by a quick-action mechanism consisting of a hollow neck which receives the relative part of the bit, which is thus locked in terms of axial movement, whereas the bit has a certain radial play. Consequently the bit does not rotate about a fixed axis but about an axis which can undergo small oscillations and movements perpendicular to itself. The mechanism which transmits movement to the drill bit can also move slightly because of intrinsic mechanical play within the mechanism. The combination of all these causes means that the drill bit undergoes a complex "wobbling" movement.
c) The hand of the operator gripping the drill is subject to muscular control, which varies from operator to operator and can also vary with time for the same operator.

From the aforegoing, and considering any cross-section through a drill bit when freely rotating, before it makes contact with the bone it describes a peripheral or enveloping circle which has a diameter greater than the true diameter of the bit at that cross-section, because of the effect of said wobbling.

Moreover when the tip of the drill bit comes into contact with the bone, no matter how expert or attentive the operator is, the bit axis is generally not exactly perpendicular to the bone surface. Consequently, even if a starter cavity is present (previously made in the bone surface), when the operator exerts a certain pressure on the bit to drill the hole, a non-axial reaction is applied to the bit, which consists of one component perpendicular to the bit axis to flex it, and a second component along the bit axis. Said flexing force has two effects, the first being the nullifying of the radial play of the mechanism which holds the bit so that said peripheral circle becomes the maximum possible, the second effect arising when play has been nullified, to deform the bit by flexure, so further increasing the diameter of the peripheral circle.

When the drill bit has initially entered the bone a cavity of previously indeterminable diameter results, this diameter being in any event certainly greater than that of the corresponding cross-section of the bit. This cavity will have a certain depth, say one or two millimetres.

It is therefore apparent that time amount of play varies in practice and cannot be controlled, and it can only be stated that the drill bit will advance through this first section in a merely "prevalent" direction, being substantially that of the theoretical axis of the bit. It is however apparent from the aforegoing that the inaccuracy will be somewhat high.

In practice, in its initial portion the cavity can be considered to consist of a series of probably irregular superposed circles of variable diameter, slightly mutually off-centre, to form a cavity extending prevalently in a certain direction.

When further pressure is applied to the drill bit it advances through the bone. Two new substantial factors now come into play to influence the operation, namely the accumulation of shavings which tend to coagulate, and the presence of that part of the cavity which has already been drilled.

The presence of shavings increases friction, to generate heat and result in further small removals of bone material from the cavity walls. The friction can increase to the extent of stopping the drill motor.

The shavings must therefore be removed whatever type of drill bit is used. This is firstly to prevent the bit heating, and secondly to allow it to move forward. They are removed by extracting the bit from the hole. Each time this is done new material is inevitably removed from the walls of the already drilled hole. That part of the hole which has already been drilled performs the important function of guiding the cylindrical body of the bit. In bits with a helical groove this body has a cutting or partly cutting effect, whereas in bits without a groove or with a vertical groove it does not cut.

If the bit body has a cutting or partly cutting effect each change in the bit direction results in a removal of material. The cavity therefore widens, so reducing its guide function. As stated, on termination of the operation the cavity is found to be formed from a series of superimposed circles of a diameter which varies within a certain range and slightly off centre to each other, to form a cavity which is therefore somewhat irregular. Of necessity the cavity will have a diameter which is greatest at its open end and smallest at its other end.

If the bit body does not have a cutting effect, the guiding efficiency of the already drilled cavity increases with increasing depth. However this does not mean that greater accuracy is obtained in drilling the cavity. In fact all the reasons which make the initial cavity wider than required (from the wobbling of the drill bit to the non-perpendicularity between the bit arid the surface of the bone) remain. In fact, a further drawback arises, and one which helically bodied bits do not possess, namely that drill bits with a cylindrical lateral surface do not have space for discharging the shavings. The bit must therefore be extracted much more frequently to clean it, this finally resulting in further widening of the cavity. The bit penetration movement is in reality helical in the direction of rotation of the drill, this movement being a combination of advancement and rotation.

Thus on termination of an in-vivo bone drilling operation conducted by normal surgical methods, the result is an approximately frusto-conical cavity of unknown diameters but certainly greater than the diameters of the drill bit used.

From tests carried out it has been found that this increase is in the order of some tenths of a millimetre, with wide variation. To make an initial approximate guess at the type of cavity obtained, one must think of a pile of discs with diameters gradually increasing upwards and decreasing towards the lower end. The discs will be slightly off-centre to each other and their centres will approximately form an irregular helical pattern. If an ideal axis is imagined passing through the centres of the two end discs, the centres of the intermediate discs will not generally lie on this axis but will lie within a certain helix about it.

If a circle is drawn having the nominal diameter of the screw (having an overall cylindrical shape) and centered on said axis, and then on this circle a further circle is drawn having the measured diameter of a certain cross-section of the cavity obtained and with its centre in its true position eccentric to the axis, the points of contact, if there are any, and the maximum distances between the two circles can be seen. If this operation is repeated for a certain number of cross-sections the number of points of contact between the screw and cavity can be determined accurately, as can the size of the non-adhering regions and their distance from the screw. This also clarifies why even with an effective diameter which is constantly greater than the nominal diameter of the drill bit there can only be a number of points of contact distributed randomly over the surface of the cavity.

If in order to verify this a drill bit is inserted into the cavity obtained, the bit may appear stable if by chance it touches the walls at a few points, but these do not ensure effective stability. What however normally happens is that the drill bit has a certain play when inserted into the cavity, showing that there is an insufficient number of points of contact.

Consequently when the cavity is finally tapped, the resultant thread will be complete in terms of depth only at the said points of contact, whereas the remainder of the thread will be only partial or indeed be completely lacking.

This however does not mean that sufficient information is available to ensure healing, given that it is not known how and in particular when the bone will reform.

The question arises as to whether it is possible to adapt operational technology, in such a manner as to obtain cavities with a precision of the order of that obtainable in the machining of the actual implants to be inserted into the cavity. The present invention shows that this is possible. In this respect it teaches that such levels of precision can be in reality obtained without having to use too complicated and very costly procedures. In this respect, with the present invention precision levels of 0.02 mm as general dimensional tolerance can be obtained, while for a series of reasons which have already been stated a precision of 0.01 mm can be obtained for surface irregularities, which can be considered optimal.

The reason for this search for precision is to reduce as much as possible, and in the theoretical limit to zero, the quantity of bone tissue which has to reform about the implant.

The problem of play between the drill bit and chuck and the intrinsic play within the drill head can only be solved by completely changing current technology. This however would result in very high cost.

It has been seen that any movement of the screw relative to the walls of the cavity which receives it has a negative effect on the repair of the bone lesion.

The object must therefore be to obtain a connection in which such relative movement is not possible. This need is currently satisfied by using a more or less forced insertion of the implant into the cavity. The bone tissue in contact with the implant is therefore compressed. This compression is the price paid by all known insertion methods which provide initial immobility of the implant. The blades or cylinders currently used for this purpose are in fat inserted with small hammer blows. In this manner a forced fit is obtained between the bone and implant by virtue of the mutual compression between certain regions of the implant and the corresponding regions of the cellular wall.

Implants formed from different elements (disk implants) utilize the traction between screw elements and prismatic bodies to obtain bone-implant adhesion areas which provide the necessary initial stability.

The screw has encountered considerable success because it enables an excellent and immediate rigid connection to be easily obtained between the implant and bone. This method has however certain negative aspects due to two basic reasons, namely the trauma (COMPRESSION) produced by the helical thread in the tissue, and the transmission to the bone, via the thread, of loads perpendicular to the screw axis.

Attempts have been made to solve both these problems by eliminating the thread and proposing cylindrically shaped implants, but these demonstrate poor initial stability (PRIMARY), require larger holes to be made, require higher bone crests and provide a lesser lateral surface for equal dimensions.

In reality the solution to the problem does not consist of attaining a stability which allows any level of bone repair, but consists of establishing best bone conditions for healing.

The best healing conditions are obtained by satisfying two general conditions:
1. Reducing surgical trauma to a minimum and eliminating debris.
2. Attaining maximum initial congruence with minimum pressure.

These two conditions result in an improvement in the progress of the reparative process, which normally involves:
1) Resorption of certain bone tissue;
2) Reshaping of other bone tissue;
3) Bone tissue neoformation.

The reduction in surgical trauma limits the necrosis of the tissue of the cellular implant wall; the elimination of debris avoids compression, resorption and infection. The fact of obtaining maximum congruence with minimum pressure results in primary stability, no bone resorption stage, no bone to be neoformed in the cortical bone part and little in the spongy part.

The female thread is currently made in the bone by two substantially different methods, namely by partial mechanical tapping (as in the Branemark method), and by self-tapping screws (as in the case of Tramonte screws).

Partial mechanical tapping involves the insertion of self-tapping screws which traumatize the bone and retain all the debris. This means that with Branemark screws the bone in contact is quickly resorbed and congruence is lost. The reparative process takes place by causes formation.

Self-tapping screws of Tramonte type allow maximum congruence between the thread and bone, but involve a forced compressive insertion which causes serious damage.

The insertion of either a self-tapping screw or a tapper into the drilled cavity causes both local and general effects in the bone, as follows:

I - Local Effects

These are caused by the following actions:
a) Cutting Action

The cutting action of the thread separates the bone tissue, damaging the calcified bone matrix, the collagen, the basic substance, the cells, the vessels and the nerves. At the commencement of the tapping operation and in the case of the self-tapping screw the cutting action causes inflammation and loss of blood. The tissue lesion results in the release of inflammatory substances (H. W. HAM—Istologia, USES 1969).
b) Compression action at interface As the tapping or the insertion of the self-tapping screw continue, the tissue is divaricated by the thread. On commencement of tapping or insertion of the self-tapping screw, if there is no counteracting element in contact with the bone surface breakage occurs by raising of the cortical bone surface, with consequent disruption of the architecture in the surrounding region. In particular, it is the tearing of the vascular connections which seriously prejudice the bone reparative process in this region. In the compagination of the tissue, the divarication necessary for the advancing movement of the thread is obtained by compression of the tissue at the interface. Under the advancement thrust the bone tissue volume corresponding to the volume of the tapper thread or of the thread of the self-tapping screw is fractured and pushed to the sides of the advancing thread. As the spongy trabecular bone tissue lies below the cortical bone, its disturbed solid part, formed of calcium salts, fills the entire available surrounding space, squeezing the vessels contained in the medulla and reducing the blood flow, with consequent ischemia, whereas its liquid part is thrust into the most peripheral trabecular region.

If the thread has a pitch which results in superposing in the spongy bone tissue regions, which then become compressed by two successive turns of the thread, a particularly negative situation arises due to the combining of harmful effects which complicate healing. In determining the pitch of the thread of self-tapping screws or of the tapper, the size of the relative core and the size of the cavity to drill in the bone, this important aspect must be taken into account.
c) Action of Heat It is well known that the heat developed in the bone during the drilling of the hole into which the self-tapping screw or tapper is to be inserted is the main cause of formation of cicatricial fibrous connective tissue, rather than new bone tissue, in the subsequent reparative process which the surgical lesion undergoes. For this reason, in drilling said hole it is advisable to use known rotary instruments internally cooled by physiological solution which in addition to cooling the drill bit also removes the bone shavings by collecting them in the grooves provided. Another method for reducing the heat produced is to limit the rotational speed of the drill to the minimum rpm which allows the hole to be drilled.

Likewise the tapping operation or the insertion of the self-tapping screw must also be very slow, so that all phenomena arising can be considered of static type, and the applied forces must be only just greater than equilibrium forces. It is essential to limit friction so as not to excessively increase temperature, which in practice must be maintained below 44° C. The rate of tapping or of insertion of the self-tapping screw must therefore be the lowest possible for screwing into the bone. This operation can therefore only be carried out manually.

The use of motorized tappers or screwdrivers does not allow easy control of the speed or consequently of the heat produced.

In conclusion, in the current state of the art, as a result of a combination of the aforesaid local effects, the damaged spongy bone tissue becomes replaced with soft cicatricial tissue, which by its nature is unable to ensure effective fixing to the screw.

II - General Effects

As is well known, tile trabecular spaces are not empty, nor is any part of the bone. The system which they form can be considered a closed hydraulic system containing a system of channels through which blood flows. Consequently the insertion of an additional volume must necessarily result in a reduction in the blood flow and an increase in the total volume of the system. Thus as in the known art the drilled hole is equal at most to the volume of the screw core, inserting the self-tapping screw or the tapper means that an additional volume is inserted into the bone tissue which is at least equal to the volume of the threads. This produces a significant increase in the internal pressure of the bone, which can easily exceed the breakage limit of the bone and cause fracture. Such fracture does not generally occur at the interface, where the aforesaid local phenomena occur, but starts from the eternal cortical bone, at the hole. Any excessive increase in the pressure within the system must therefore be avoided.

There is a second effect which produces a pressure increase within the bone. This is generated by the insertion of a self-tapping screw or of a tapper of known type. This is because from the very commencement of their insertion these close the hole in the bone, from which the blood should emerge. This blood is therefore pushed to the base of the hole to further increase the internal pressure of the bone, so that said fracture risk increases.

The object of the present invention is to overcome the aforesaid drawbacks of known bone screws and of their methods of application, by providing a screw device for fixing prostheses to bones, a method for applying the device, and the instrument for effecting the application, such as to result in spontaneous repair (by creeping substitution) of the lamellar bone tissue around the screw, the screw becoming thus securely and permanently fixed in the bone. To obtain healing by creeping substitution, a method of bone repair essentially identical to bone rearrangement, the quantity of blood coagulum present at the surface of the screw implant according to the present invention must be minimal. This is because blood coagulum converts into mature lamellar bone very slowly (6–12 months in man), by a self-limiting process. This latter characteristic means that ossification of the coagulum may not go to completion, and instead give rise to the formation of fibrous tissue unsuitable for supporting loads.

To enable creeping substitution to take place it is also essential that the vascular channels in the necrotic lamellar bone are not destroyed, and thus the pressure exerted during screwing must be a minimum.

The present invention proposes firstly to substantially eliminate the blood coagulum between the calcified bone and the implant by obtaining the maximum possible congruence or adhesion between the bone tissue and the relative parts of the screw, without any pressure being exerted which could irreparably damage the lamellar bone.

In particular, it is essential that the cavity formed in the bone has a degree of precision substantially higher than that currently obtainable in the known art, so as to reduce to a minimum the amount of bone tissue which has to reform. The screw must also have a shape which reduces the amount of bone tissue to be reformed to a minimum.

During healing, in order for the necrotic lamellar bone tissue transformation to take place by creeping substitution (which preserves the special mechanical characteristics of lamellar bone and takes place within 6–12 weeks), it is essential to prevent the aforesaid phenomena occurring. In particular any resorption of marginal bone or bone debris must be prevented. This ensures primary stability, which is essential. In this case, even during the healing period, during which for obvious reasons one tries not to load the screw, this latter is able to support those small loads which accidentally but almost inevitably tend to act on it, without any negative consequences arising.

The screw device according to the present invention comprises a neck and a threaded shank, and is characterised in that the threaded shank of the screw has a core of overall frusto-conical shape, the screw core being cylindrical and having a diameter equal to or just greater than the maximum diameter of the thread on the shank of the screw, and the thread being of two different types, namely a first thread of large pitch suitable for fixing into the trabecular bone tissue and extending along that part of the shank which is designed to make contact with said trabecular tissue, and a second thread, which can be of the self-tapping type, and intended to fix into that cortical part of the bone opposite the part into which the screw is inserted, said second thread having a number of starts which is a multiple of that of the first thread.

In contrast to a screw with a cylindrical core, a screw with a frusto-conical core, because of its particular geometrical shape and if associated with a corresponding suitable frusto-conical cavity of adequate precision, reduces the quantity of bone tissue to be reformed practically to zero, with maximum congruence obtained between the screw and cavity.

In addition because of the double type of thread, the described screw can fix effectively into both the trabecular bone tissue and into the cortical bone.

The fact that the screw neck, which when the screw is inserted lies only in the cortical bone on the screw insertion side, has a diameter greater or in the limit equal to that of the thread, means that the hole made in the bone must have a first portion, in practice equal only to said cortical bone, having a diameter at least equal to the neck diameter. Thus on inserting the self-tapping screw or tapper the cortical bone is not ruined.

If a fixing means or the like is present in contact with that cortical bone surface at which the screw is inserted to act as a counteracting means (for example in the case of screws for orthopedic use a prosthesis or a bone synthesis means resting against the surface), the screw according to the invention can comprise on the lateral surface of the screw neck a third thread of the same type as said second thread.

In this respect it has been found that the existence of said counteracting means in contact with the surfaces of said cortical bone prevents the lifting and destruction of the most outer part of the cortical bone, which could happen when said third self-tapping thread penetrates into the cortical bone if such a counteracting means were absent. A situation of this type occurs for example when a plate has to be applied for the synthesis of bone fractures.

In the particular stated case a fixing is therefore also obtained at the cortical bone via the screw neck, to obtain the best possible fixing for the screw in the bone.

To obtain the best result from the use of the screw device according to the invention a particular method of application must be followed for the device. This method also forms part of the present invention and enables a cavity to be obtained having dimensions substantially more precise than that obtainable by the known art and such as to reduce the quantity of bone tissue to be reformed to a minimum.

Specifically, the method for applying the screw device of the invention consists of:

forming a precision hole in the bone in the position in which said screw device is to be inserted, the hole comprising: a first more outer cylindrical portion to receive the screw neck, this first portion having a diameter equal to or preferably slightly less than that of the non-threaded neck of the screw, or slightly greater than the maximum core diameter of the neck if this latter is threaded; a second more inner frusto-conical portion of transverse dimensions equal to or preferably slightly less than those of the core of the first screw shank part carrying said first type of large-pitch thread; and a third portion extending along the remaining length of the screw shank, this third portion being relative to said second type of screw thread and of transverse dimensions slightly greater than those of the core of that shank part with said second type of thread;

tapping the said second portion of the hole to obtain in it a female thread suitable for receiving the said first screw thread;

if said second screw thread is not of self-tapping type, tapping said third portion to obtain in it a female thread suitable for receiving said second screw thread;

completely screwing said screw into the tapped hole.

This method of application results in maximum congruence between the screw and bone.

The said hole provided in the bone can also be a through hole if appropriate.

The present invention also relates to a cutter and reamer for forming said precision hole, and a precision boring method using said cutter and reamer.

Specifically, the cutter according to the invention is cooled by sterile liquid which also performs the function of removing the bone shavings which form, and is characterised by having its cutting part in the shape of an inverted "wedding cake". By this term, which immediately enables the shape of the cutter to be visualized, it is meant that the cutter consists of a number of coaxial cylindrical bodies rigid with each other, their diameter decreasing towards the tip of the cutter.

The manual reamer according to the invention is of such form and dimensions as to enable the final hole to be obtained with the required precision, ready for tapping, and is characterised by having a relief angle suitable for cutting bone tissue.

Conveniently, the reamer comprises means for conveying isotonic liquids into the cavity formed in the bone, to facilitate the operation. The purpose of such liquids is to reduce bone necrosis.

The means for conveying nutrient liquids can simply consist of a coaxial channel passing through the entire reamer, in communication with a device for feeding isotonic liquids and with lateral apertures provided between the reamer cutting edges, to enable the isotonic liquid to make contact with the tissues concerned.

The method for forming said precision hole for the insertion of a screw device according to the present invention consists of:

forming with the inverted "wedding cake" cutter a cavity with steps having diameters less than or at most equal to those of the required precision hole;

then, by means of said reamer, manually reaming the thus formed stepped cavity to obtain the required precision hole ready for tapping.

It has been found that the best results are obtained when both the (unthreaded) neck of the screw and the core of the first shank part of the screw have diameters which are slightly greater by a few microns than those of the relative hole. In this case the screw slightly compresses as it is screwed in, but without causing the damage previously described under point I(b). In this manner maximum congruence is obtained between the screw neck and thread on the one hand, ad the bone tissue on the other, to also produce minimum bone damage.

It has also been found advantageous to screw the screw slightly further in once it has reached its final position in the cavity. This provides maximum adherence between the screw frustum or core and the cavity.

To form the large-pitch female thread in the side walls of the second hole portion to receive the first type of screw thread, the tapper according to the invention is used, having a tapping thread with a maximum diameter not exceeding that of the screw neck, this tapping thread having the same number of starts and the same pitch as the first screw thread, and extending for the same length as said first screw thread, the end part of the tapper, of length substantially equal to that of the second screw thread, being free of tapping threads and having transverse dimensions not exceeding those of the corresponding third portion of the hole if said second screw thread is of the self-tapping type, whereas said end part of the tapper has a tapping thread with the same number of starts and the same pitch as the second screw thread if this second thread is not self-tapping; the tapper having at least one discharge means to allow escape of the organic liquids. In one embodiment of the tapper according to the present invention the discharge means can be a coaxial channel communicating with apertures which open between the tapper threads. In a modified embodiment of the tapper according to the invention the discharge means are one or more longitudinal lateral grooves extending along the entire length of the tapper to interrupt all of its threads and partly involve the core of the lapper. The outer edges of each groove are conveniently rounded to reduce damage to the bone tissue to a minimum.

Preferably the directrices forming the frusto-conical core of the second screw thread are parallel, but internal, to the directrices forming the core of the first thread, so that a small annular step is present between the two surfaces.

When the screw has been inserted there is therefore an annular space between the core of the second thread and the corresponding side wall of the hole. This space acts as a compensation space which is at least partly filled by cortical bone bone tissue which is plastically deformed following introduction of the screw into the third hole portion if the screw if the second thread is self-tapping, or of the threaded end part of the tapper if the second screw thread is not self-tapping.

This compensates that thread volume which penetrates into the cortical bone, so that no dangerous pressure increase is created in the bone.

In the relative shank part of the second screw thread there can be provided at least one longitudinal groove having the double purpose of providing further compensation space for any other pressure increases which may arise, and of providing a region for collecting any bone shavings. Such pressure increases can be generated by fluid present under the tip of the screw, and which having no means of escape could undergo compression during screwing, with the stated consequent drawbacks.

Said vertical groove also acts as an anti-unscrewing device because new cortical bone tissue forms in it to prevent unscrewing.

Thus in cases in which the screw is to be removed after a certain time period this groove must not be provided.

For the first type of screw thread an annular compensation space as provided for the second self-tapping thread is not essential, because of the different nature of the bone tissue concerned, ie trabecular. As stated, the tapper for forming the female thread for receiving the first screw thread cuts and laterally displaces the solid part of the spongy bone tissue, which fills the available adjacent space.

As also stated, the purpose of the discharge means provided in the tapper for the liquids contained in the bone is to enable both the blood emerging from the surgical wound and that liquid fraction displaced by the formation of the female threads to escape. This enables local effects (which have already been mentioned) to be controlled to the desired degree and also inhibits the already mentioned negative general effects.

It has been stated that the discharge means can be grooves provided in the tapper. It should be noted that normal tappers for mechanical use also comprise longitudinal discharge grooves which interrupt the tapping threads and also involve their core. These grooves have however a different purpose. In these, the edges of the longitudinal grooves must be properly sharp in order to cut the material in which the female thread is to be formed. The purpose of these grooves is to allow collection and removal of the shavings formed by the action of the groove cutting edges against the hole wall.

In contrast in the present case, as the formation of shavings during the making of the large-pitch female thread is to be prevented and the said trabecular tissue compression is to be limited, the edges of the longitudinal groove are rounded. In tapping with the tapper according to the invention there is therefore no removal of bone tissue but only the removal of an equivalent volume of organic fluids. The trabecular tissue is therefore only cut and dislodged by the tapper threads without any pressure increase occurring. The spongy bone tissue therefore only undergoes displacement of the said solid and liquid, which does not prejudice the crawling substitution reparative process of the new lamellar bone tissue in the surrounding regions damaged by the tapping operation.

In penetrating the spongy bone tissue the large-pitch thread of the tapper must damage this tissue as little as possible. particular, the crest of the first turn of the tapping thread must be pointed to allow optimum tissue cutting action. A convenient cross-sectional shape for the other turns of the tapper thread could therefore be trapezoidal without sharp edges, this being easily obtained mechanically. The first thread of the screw can also have threads of trapezoidal cross-section. This shape enables external loads perpendicular to the tapper axis to be absorbed without any cutting action occurring, and which would in contrast occur with pointed crests.

For the second screw thread involving the cortical bone, said problems are not so stringent, so that the cross-section of the relative thread can conveniently be triangular but with a rounded crest to avoid as much as possible any cutting action or dangerous load concentration should a force with a component perpendicular to the screw axis act on the screw.

The same applies to the tapping thread on the end of the tapper if the second screw thread is not self-tapping.

The invention will be more apparent from the following description of two embodiments of the screw according to the invention, of the hole for the screw, of the cutter and reamer for obtaining the required hole precision, and of the corresponding tapper.

Reference is made in this description to the accompanying drawings, in which.

Figures 1, 2:
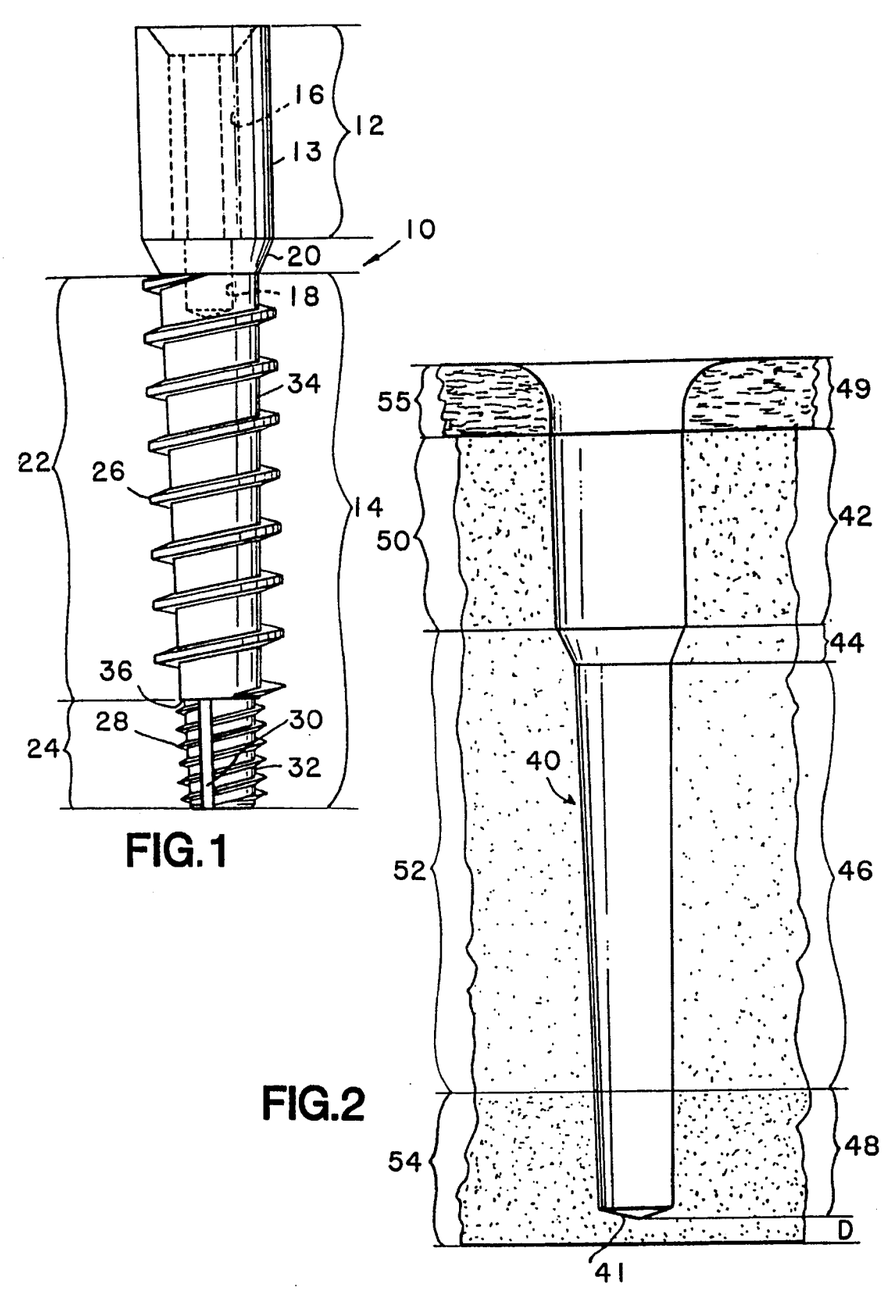
FIG. 1 is a side view of a screw according to the invention, particularly suitable for odontology, of the type comprising a self-tapping second thread.
FIG. 2 is an axial longitudinal section through the hole for receiving the screw of FIG. 1, before the hole has been tapped.

From FIG. 1 it can be seen that the screw 10 consists of two distinct basic parts, namely a cylindrical upper neck 12 and a threaded shank 14.

The threaded shank 14 is coaxial to the neck 12 and integral with it, and connects to the neck 12 via a short frusto-conical connecting section 20. This latter can however be absent, the frusto-conical surface of the screw core then extending directly from the periphery of the base of the cylindrical neck 12.

The upper portion of the cylindrical neck 12 is intended to project beyond the bone, whereas the rest of the neck 12 is surrounded by the cortical bone with the screw inserted.

A cylindrical rather than frusto-conical shape has been chosen for the screw neck 12, so that when under load the neck does not transmit axial loads to the adjacent cortical bone, but is able to transmit to the cortical bone any loads perpendicular to the axis of the screw 10 via its lateral surface 13 which is surrounded by it when the screw has been applied.

In the free upper surface of the cylindrical neck 12 there is an axial prismatic cavity 16 (shown by dashed lines in FIG. 1) to receive a suitable tool (Allen key or the like), not shown on the drawings, to enable the screw 10 to be manually screwed into the bone and to allow the screw to subsequently receive dental prostheses. These latter can for example comprise a pin-stump for prosthetic application by the method of Dr. Vrespa (Cenacolo Gruppo Italiano Studi Implantari, Bologna, November 187; Atti Congresso Internazionale GISI, May 1988). At the base of the prismatic cavity 16 there is a threaded or non-threaded axial hole 18 (shown dashed in FIG. 1), for fixing to the screw a known healing plug (not shown) or whatever else may be required.

The presence of the two cavities 16 and 18 allows a mesostructure to be applied by screwing or cementing depending on the choice made and the requirements of the particular case.

The shank 14 comprises two coaxially, aligned parts 22 and 24 forming a single piece ad having two different types of thread. Specifically, a first cylindrical single-start thread 26 of large pitch is provided on the upper part 22 of the shank 14. The first thread 26 is suitable for fixing into the spongy bone tissue, the relative thread having a trapezoidal cross-section with rounded edges. In the case shown in FIG. 1 the helical crest of the turns of the first thread 26 lie on a cylindrical surface having a diameter equal to the diameter of the screw neck 12, the outer diameter of the first thread thus being constant throughout its entire length. Consequently the height of the thread increases from the top downwards. In the case in which the frusto-conical connection 20 is not provided and if said surface is still cylindrical, the thread height starts from zero at its highest point.

Returning to the embodiment shown in FIG. 1, on the lower part 24 of the shank 14 there is a second thread 28 with three starts, each with the same pitch as the first thread 26. The second thread 28 is self-tapping. The thread turns are of triangular cross-section with a rounded crest. The thread height is constant along the entire thread. The thread crests lie on a frusto-conical surface parallel to that of the core 32 of the second thread. Because it has three starts this latter acts from the fixing viewpoint substantially as a thread having a pitch equal to ⅓ of the effective pitch. This makes the thread suitable for fixing into the cortical bone, and in this specific case into the cortical bone opposite the point of introduction of the screw.

The lengths of the various component parts of the screw are obviously such that when the screw is inserted into the bone the screw neck 12 lies mainly within the cortical bone on the side from which the screw is inserted, the intermediate part 22 of the shank 14 comprising the first thread 26 lies within the trabecular bone tissue, and the end part 24 of the shank 14 which contains the the second thread 28 lies mainly within the opposite cortical bone. In practice the screw neck 12 and the second thread 28 may lie slightly within the trabecular bone tissue region as it is difficult to previously know the exact thickness of the cortical bone.

As can be seen from FIG. 1, the part 24 of the shank 14 comprises a vertical groove 30 which interrupts the thread 28 and lies partly within the core 32.

The purpose of the groove 30, which can however also be absent, has already been stated.

From FIG. 1 it can be seen that both the core 34 of the upper part 22 of the shank 14 and the core 32 of the lower part 24 are frusto-conical (the relative lateral surfaces being parallel), but with a small step 36 between them.

The method of application of the screw of FIG. 1 and the tools for the purpose will now be briefly described, with particular reference to the making of the hole into which said screw is to be inserted.

The first operation consists of drilling in the bone a precision hole 40 shaped as in FIG. 2.

Figures 9, 10:
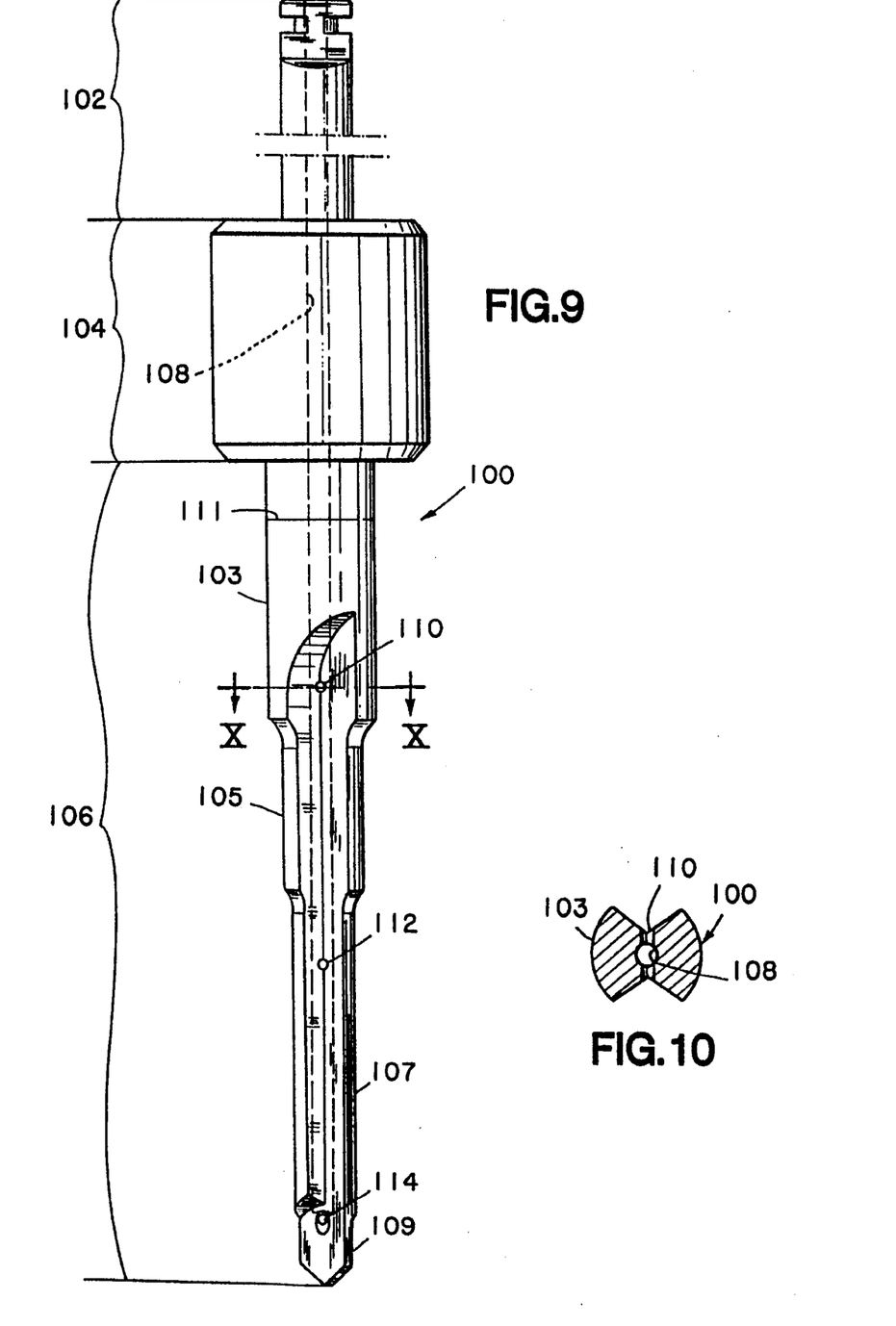
FIG. 9 is a side view of time inverted "wedding cake" cutter according to the present invention.
FIG. 10 is a cross-section therethrough on the line X—X of FIG. 9.

To do this the so-called inverted "wedding cake" cutters of the present invention are used. One of these cutters is shown in FIGS. 9 and 10. The cutter 100 consists of a shank 102 of conventional shape, a spacer portion or extension 104, and a cutter portion 106. The shank 102 is connected into the already mentioned quick-connection mechanism of the drill. The purpose of the extension 104, which is of suitable length, is merely to enable the cutter portion 106 to reach the required point, for example when a hole is to be drilled between two teeth adjacent to a missing tooth. If this requirement does not arise then the extension 104 can be absent.

As can be seen from FIGS. 9 and 10, the actual cutter part 106 consists substantially of three coaxial cutting bodies 103, 105 and 107, which are rigid with each other and arranged to produce three hole portions of circular cross-section and having a diameter which respectively decreases towards the interior of the bone.

The cutter 100 terminates with a tip 109 of conventional type and comprises an axial channel 108 communicating with the apertures 110, 112 and 114 visible in FIG. 9. The channel 108 enables the iosotonic cooling liquids to be discharged during bone drilling. Preferably a circular line 111 is engraved or otherwise reproduced on the cutting body 103 to visibly indicate the exact level to which the cutter 100 must penetrate into the bone. When the line 111 has reached the level of the bone surface it is therefore certain that the cutter has reached the required depth.

When a stepped hole of the stated type has been obtained in the bone by one advancement of the cutter 100, the hole is enlarged by means of a manual reamer of the present invention, to obtain a frusto-conical hole of the required precision (FIG. 2). A reamer of this type is shogun in FIGS. 11 and 12.

Figures 6, 7, 11, 12:
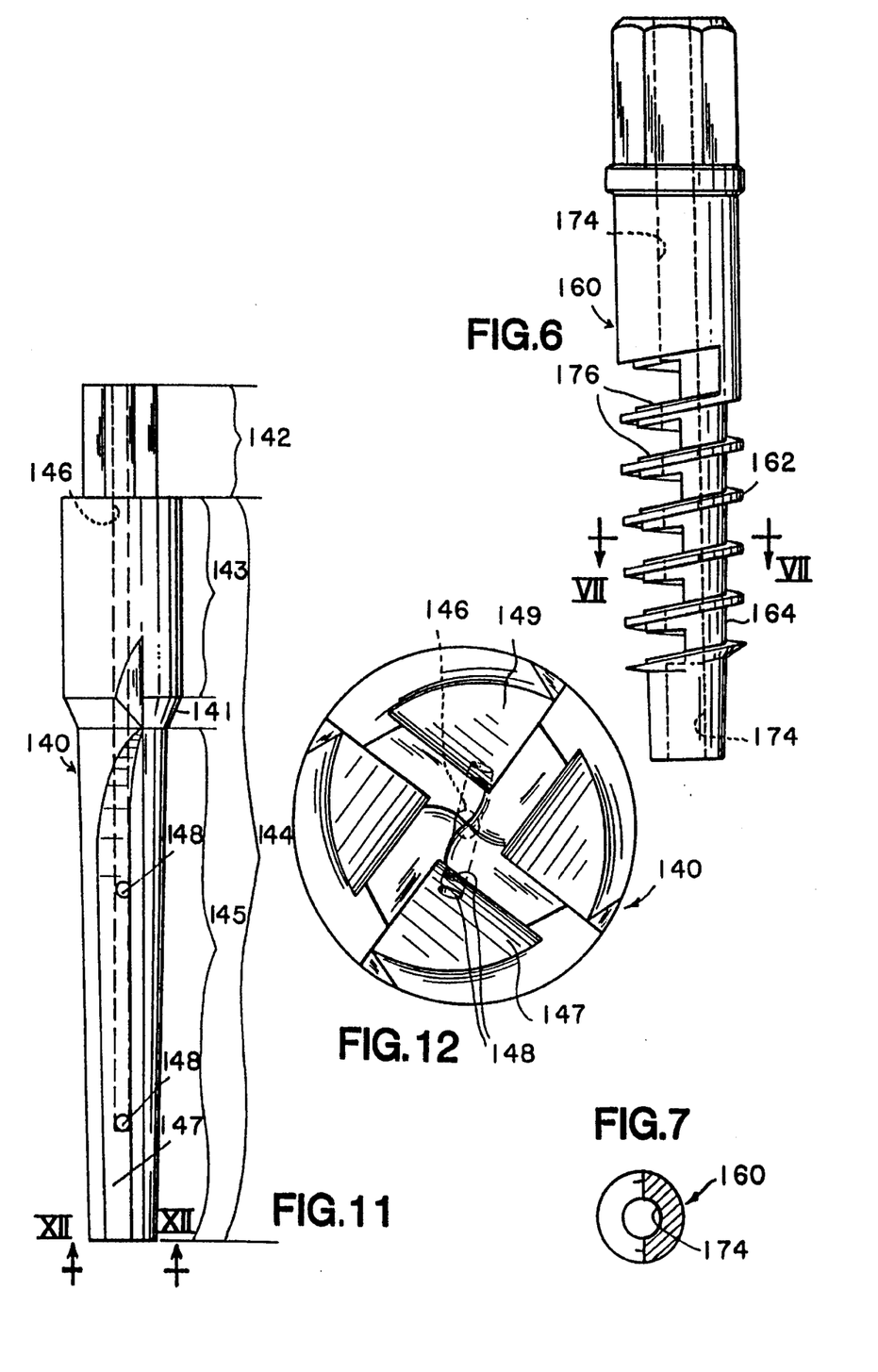
FIG. 6 is a side view of a second embodiment of the tapper according to the invention.
FIG. 7 is a cross-section therethrough on the line VII—VII of FIG. 6.
FIG. 11 is a side view of the reamer according to the present invention.
FIG. 12 is an enlarged bottom view thereof on the line XII—XII of FIG. 11.

As already stated, to obtain the desired results the reamer 140 must necessarily be operated manually.

The reamer 140 comprises a shank part 142 of hexagonal cross-section to be engaged by a suitable tool for the manual reaming of said stepped cavity, plus a reamer part 144, which has a relief angle suitable for cutting the bone tissue. The reamer part 144 is itself divided into two sections, namely a first section 143 for producing a cylindrical hole portion and a second section 145 for producing a frusto-conical hole portion.

In the specific case of FIG. 11, the first section 143 connects to the second section 145 via a frusto-conical connection 141. As stated, the reamer 140 also comprises an axial channel 146 which passes completely through it and communicates with lateral apertures 148 provided between the cutting edges. In the specific case of FIGS. 11 and 12 the lateral apertures 148 are four in number, two in the groove 147 and two in the opposite groove 149. The isotonic liquid is fed through the channel 146 to reduce bone necrosis.

When said reaming is complete a hole is obtained of the type shown in FIG. 2. This hole can also be a through hole or can stop at a certain distance D from the outer surface of the opposite cortical bone.

The first portion 42 of the hole 40 is cylindrical and has a diameter less by a few microns than the diameter of the cylindrical neck 12 (FIG. 1) of the screw. The height of this first portion 42 is equal to or slightly greater than the thickness of the cortical bone 50, and in any event sufficient for receiving that part of the neck 12 of the screw 10 which is intended to enter the bone.

The hole 40 proceeds inwards via a short frusto-conical connection portion 44, corresponding to the frusto-conical section 141 of the reamer 140 (FIG. 11) and to the frusto-conical portion of the screw 10 (FIG. 1). It connects the first section 42 to the second frusto-conical section 46. This latter has diameters less by a few microns than the diameters of the core 34 of the first part 22 of the shank 14 of the screw 10.

The hole 40 terminates with a third portion 48, which is nothing other than the prolongation into the opposite cortical bone 54 of the directrices of the second hole portion 46.

In the aforesaid case in which the screw 10 (FIG. 1) does not have the frusto-conical connection portion 20, the hole will also not have said connection portion 44, the second frusto-conical portion of the hole then extending directly from the base perimeter of the first cylindrical portion 42 of the hole.

Likewise, the reamer 140 (FIG. 11) will also not have the frusto-conical connecting section 141.

Conveniently, the third portion 48 of the hole 40 is slightly longer (for example by 1 mm) than the corresponding lower part 24 of the shank 14 of the screw 10 (FIG. 1). The purpose of this is to prevent destruction of the female thread in the bone by any over-tightening of the screw, which could occur if the two said lengths are equal. In this respect any further advancement of the screw is prevented by the base 41 of the hole 40.

The slightly longer length of the hole 40 results in adhesion between the conical cavity and the core of the screw. This also compensates for tolerances.

In the specific case of dental screws, the upper cortical bone 50 becomes covered by the gingive 55 (see FIG. 2), so that this latter has to be perforated by conventional tools before proceeding with the drilling. The hole will therefore also comprise an upper gingival portion 49.

When the hole 40 has been made, a female thread (not shown in the figures) is formed in the side wall of its second portion 46 to receive the first thread 26 of the shank 14 of the screw 10. This is obtained using the tapper 60 shown in FIG. 3. To increase adhesion between the screw 10 and the new bone tissue which has to reform about the screw, the first part 22 of the shank 14 and the respective part of the neck 12 are normally coated with titanium in known manner by plasma spray treatment, which slightly increases its dimensions.

Figures 3, 4, 5, 8:
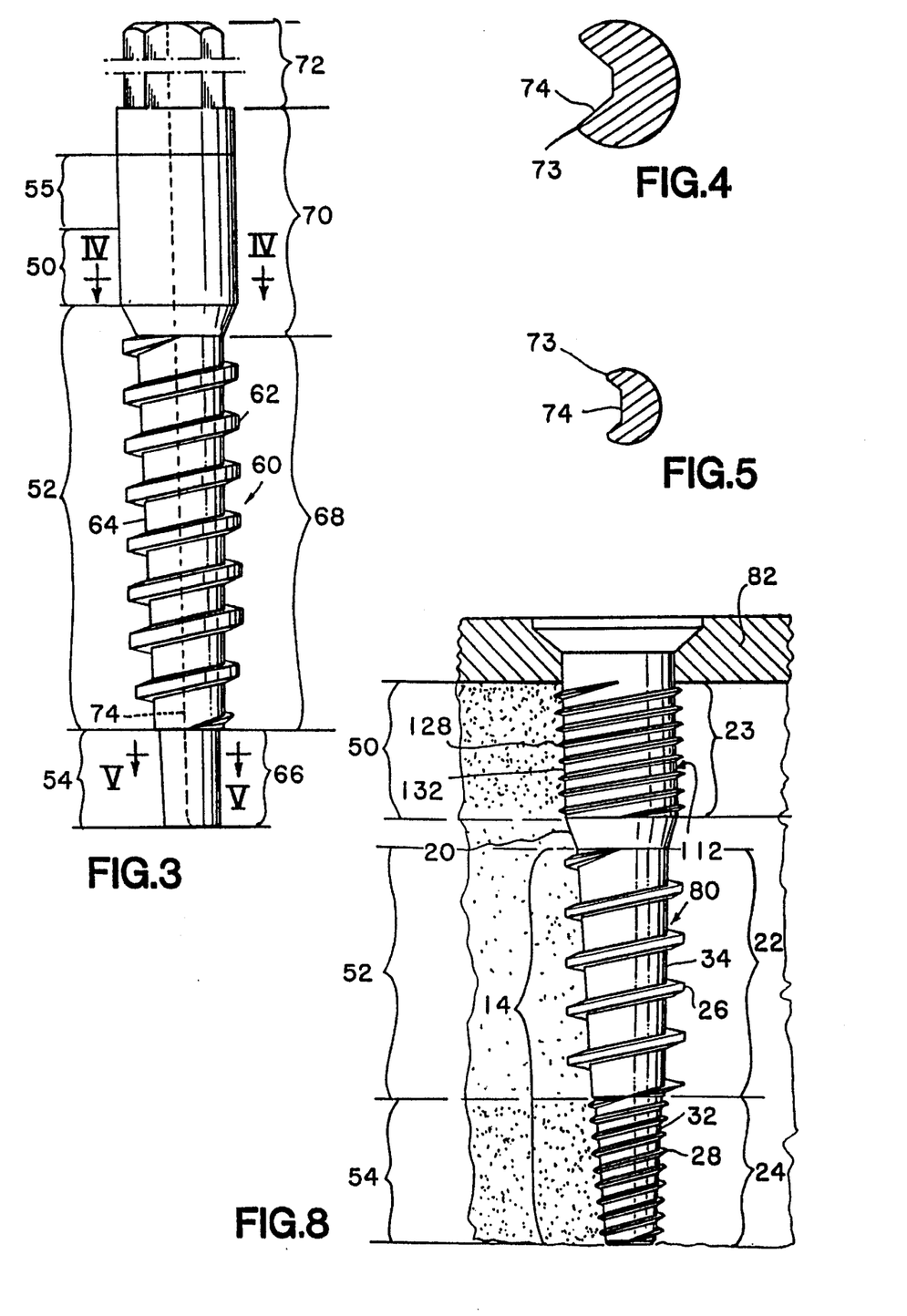
FIG. 3 is a side view of a first embodiment of the tapper according to the invention for tapping the hole of FIG. 2, the tapper having an unthreaded end part.
FIG. 4 is a cross-section therethrough on the line IV—IV of FIG. 3.
FIG. 5 is a cross-section therethrough on the line V—V of FIG. 4.
FIG. 8 is a side view of a screw particularly suitable for orthopedics.

Consequently the dimensions of the tapping thread 62 and of the core 64 of the part 68 of the tapper 60 must be proportionally increased with respect to the dimensions of the bare screw, as must the dimensions of the parts 46, 42 and 44 of the hole 40. The lower frusto-conical part 66 of the tapper 60 is unthreaded, it has the same length as the corresponding second part 24 of the shank 14 of the screw 10, and at most has time same transverse dimensions as the core 32 of said part 24 of the screw.

The tapper also comprises an upper part 70 substantially analogous to the neck 12 of the screw 10, the part 70 upperly comprising a projection 72 having a polygonal cross-section for engagement by a suitable tool (not shown) to enable tile tapper 60 to be inserted.

This latter comprises a longitudinal groove 74 of substantially trapezoidal cross-section extending along the entire tapper (see also FIGS. 4 and 5), its purpose having already been stated. It will be noted that the edges 73 of the groove 74 are rounded, for the previously stated reasons.

FIGS. 6 and 7 show a modification of the tapper according to the invention which has proved particularly convenient. The tapper 160 is particularly suitable for tapping holes for receiving screws without the connection portion 20, so that the relative precision hole will be without tile portion 44. The only true difference compared with the tapper 60 of FIGS. 3 to 5 is that instead of the longitudinal groove 74 (FIG. 3) for discharging the organic liquids there is a coaxial circular channel 174 which passes longitudinally through the entire tapper 160. This channel communicates with the outside not only at its two ends but also via the series of apertures 176 provided in the core part 164, each aperture opening between two successive turns of the tapping thread 162.

The dimensions of the tapper 160 of FIGS. 6 and 7 do not correspond to those of the screw of FIG. 1, as it relates to a shorter screw without the connection portion 20, as stated. When the hole 40 has been tapped, the screw 10 is screwed into it, its second self-tapping thread 24 penetrating securely into the opposite cortical bone 54 (FIG. 3).

After a suitable time period, required for crawling substitution in the cortical bone and the formation, of primary bone in the spongy part, new bone tissue reforms in contact with the screw to ensure its stability with time.

FIG. 8 shows a modification of the screw according to the invention which is particularly suitable for orthopedics, for example for fixing a plate to a femur. The screw 80 is shown in FIG. 8 already inserted into the bone. It differs from the screw 10 of FIG. 1 only by the presence of a third self-tapping thread 23 provided on the lateral surface of the screw neck 112.

The third thread 23 can be provided only if a counteracting element 82 is present, such as a plate resting on the surface of the femur cortical bone 50. The plate 82 prevents lifting and destruction of the surface layer of the cortical bone 50 when the self-tapping thread 23 grips the cortical bone 50

The third thread 23 could also be not of self-tapping type. In this case, in the first portion 42 of the hole 40 a relative female thread is formed by a suitable tapper (not shown). The relative hole portion corresponding to the neck 112 of the screw 80 is consequently given a slightly larger diameter than the relative core 132 of the thread 23 of the screw 80, but less than the outer diameter of the thread 23, for the same reasons as stated for the hole corresponding to the second thread 28.

As will be immediately apparent, the orthopedics screw 80 results in optimum stable fixing to the bone.

I claim:

1. A screw device for fixing a prosthesis to a bone, the device comprising:
   a substantially cylindrical neck having a diameter; and
   a shank having a core of generally frusto-conical shape and thread on the core, the thread having a diameter equal to or less than the diameter of the neck, the thread comprising a first thread portion of large pitch, and having a number of starts the first thread portion being suitable for fixing to trabecular bone tissue and a separate second thread portion of smaller pitch adjacent the first thread portion and suitable for fixing into a cortical part of the bone, the second thread portion having a number of starts which is a multiple of the number of starts on the first thread portion.

2. A screw device as claimed in claim 1 wherein the second thread portion of the shank is self-tapping.

3. A screw device as claimed in claim 1 wherein the first thread portion is of substantially trapezoidal cross-section and the second thread portion is of substantially triangular cross-section.

4. A screw device as claimed in claim 1 wherein the first thread portion has an outer diameter which is constant.

5. A screw device as claimed in claim 1 wherein the second thread portion has three times as many starts as the number of starts on the first thread portion.

6. A screw device as claimed in claim 1 wherein the first thread portion is a single-start thread, and the second thread portion is a three-start thread.

7. A screw device as claimed in claim 1 wherein the neck has a surface which comprises a third thread portion which is self-tapping type.

8. A screw device as claimed in claim 1 wherein the neck has an end including a first hole therein for receiving a prosthetic pin.

9. A screw device as claimed in claim 8 wherein the neck has a cavity therein substantially coaxial with the hole, the cavity receiving a tool to facilitate fixing of the screw device to the bone.

10. A screw device as claimed in claim 1 wherein the neck has a cavity therein for receiving a tool to facilitate fixing of the screw device to the bone.

* * * * *